United States Patent [19]

Amelung

[11] Patent Number: 5,279,159
[45] Date of Patent: Jan. 18, 1994

[54] MEASURING VESSEL

[75] Inventor: Rolf Amelung, Lemgo, Fed. Rep. of Germany

[73] Assignee: Heinrich Amelung GmbH, Lemgo, Fed. Rep. of Germany

[21] Appl. No.: 20,616

[22] Filed: Feb. 22, 1993

[30] Foreign Application Priority Data

Feb. 25, 1992 [DE] Fed. Rep. of Germany ....... 4205618

[51] Int. Cl.$^5$ ...................... G01F 19/00; G01N 1/02; B01L 3/00
[52] U.S. Cl. ..................... 73/426; 604/403; 73/864.51; 73/864.91
[58] Field of Search ................ 73/426, 864.51, 864.91; 604/403, 404

[56] References Cited

U.S. PATENT DOCUMENTS

| | | | |
|---|---|---|---|
| 3,184,974 | 5/1965 | Riley | 73/426 |
| 3,800,780 | 4/1974 | Elliott | 604/404 |
| 3,902,477 | 9/1975 | Gerarde | 604/403 |
| 4,235,839 | 11/1980 | Vesterberg | 73/864.51 |
| 4,783,305 | 11/1988 | Forrest | 73/426 |
| 4,946,651 | 8/1990 | Liston et al. | 73/864.91 |
| 4,986,965 | 1/1991 | Ushikubo | 73/864.91 |

FOREIGN PATENT DOCUMENTS

| | | | |
|---|---|---|---|
| 2332493 | 1/1974 | Fed. Rep. of Germany | 604/404 |
| 2558311 | 7/1976 | Fed. Rep. of Germany | 73/864.51 |
| 1005744 | 3/1983 | U.S.S.R. | 73/864.51 |
| 2183159 | 6/1987 | United Kingdom | 604/403 |

*Primary Examiner*—William A. Cuchlinski, Jr.
*Assistant Examiner*—Diego F. F. Gutierrez
*Attorney, Agent, or Firm*—Feiereisen & Kueffner

[57] ABSTRACT

A measuring vessel for containment of liquids to be tested such as blood, blood plasma or the like includes a rectangular well with an inlet opening at one end thereof and with another funnel-shaped end which is connected to a tubular member closed by a cylindrical bottom with an inwardly projecting central pin to define a track for a spherical body for allowing determination of the coagulation behavior of the liquid. The tubular member includes at least two parallel side faces which extend over nearly the entire length of the tubular member. A footing is fixed to the tubular member in elongation of each broadside of the well for enabling a secure placement of the measuring vessel.

7 Claims, 1 Drawing Sheet

100 # MEASURING VESSEL

BACKGROUND OF THE INVENTION

The present invention refers to a measuring or graduated vessel for receiving liquids to be tested such as blood, blood plasma or the like.

German patent specification DE-PS 29 37 195 discloses a measuring vessel with a circular bottom provided with a projecting central limiter pin and forming a track for a spherical body by which the coagulation behavior of blood can be mechanically determined in a very precise manner. In addition to this analytical process, photometric analysis is used to carry out certain measurements of blood, blood plasma or the like. In order to conduct a proper photometric analysis, it is necessary to enable an unobstructed passage of light emitted from a light source through the wall of the measuring vessel. The cylindrical configuration of the conventional measuring vessel is, however, unsuitable for photometric measurement as the curvature of the wall deflects incident light rays, leading to inaccurate results.

In addition, the conventional measuring vessel conflicts with an automatic analyzing process. Especially in connection with a photometric analysis, the cylindrical configuration of the measuring vessel complicates an exact positioning of the measuring vessel relative to the light source. This, however, is a precondition for an unobjectionable measurement. Apart from complicating the automatic feed and positioning of the measuring vessel, the cylindrical configuration also conflicts with an optimal utilization of the available storage space in a storage box which generally contains a plurality of measuring vessels and is transported in its entirety to a consumer for automatic withdrawal of a measuring vessel. In order to enable accommodation of a greatest possible number of measuring vessels, it necessarily follows that the existing space of the storage box should be utilized in an optimum manner. Evidently, the cylindrical configuration of the measuring vessels is in conflict with such a demand.

SUMMARY OF THE INVENTION

It is thus an object of the present invention to provide an improved measuring vessel obviating the aforestated drawbacks.

In particular, it is an object of the present invention to provide an improved measuring vessel by which a mechanical measurement in accordance with the ball method as well as a photometric analysis of the liquids being tested is possible and which allows an automatic transport to an analyzer while still utilizing the available space of a storage box in an optimum manner.

These objects and others, which will become apparent hereinafter, are attained in accordance with the present invention by providing the measuring vessel with a well or compartment of generally rectangular cross section to define parallel broadsides forming planar contact surfaces, with the well having one end defining an inlet opening and another end which is shaped in form of a funnel and connected to a tubular member closed by a cylindrical bottom and having at least two parallel side faces which extend over a major part of the length of the tubular member, with the tubular member being connected with a support structure in form of a footing for enabling secure placement of the measuring vessel.

The provision of a measuring vessel in accordance with the present invention allows application of photometric analysis over the entire spectral range, in particular for chromogen substrates, enzyme-kinetic and end point determinations. While at least two opposing parallel side faces of the tubular member extend almost over the entire length of the tubular member, the side area of the tubular member, adjacent to the bottom is of cylindrical configuration. In this manner, the area above the central limiter pin can be utilized for photometric analysis while the lower bottom area is suitable for the analysis according to the ball method.

The measuring vessel according to the present invention thus allows a combined analysis of liquids, and moreover is advantageously usable for an automatic analyzing process. The rectangular configuration enables an optimal placement of the measuring vessel inside a storage box which contains a great number of such measuring vessels and is introduced in an analyzer for automatic supply of measuring vessels. Suitably, two neighboring measuring vessels abut each other along opposite planar contact surfaces which are formed by the parallel broadsides of the well.

The rectangular configuration of the measuring vessel and the provision of a support structure for the vessel, preferably in form of a laterally arranged footing extending from each broadside of the well along the funnel section and tubular member, permits an accurate positioning and secure withdrawal of the measuring vessels from the storage box, with the footing ensuring the stability of the measuring vessels during their withdrawal.

Suitably, the measuring vessel is made of transparent plastic material. Since manufacturing reasons dictate to locate the sprue on the exterior of the bottom of the measuring vessel, it is preferred to slightly extend the footings beyond the bottom in order to prevent a hooking of the vessel by the sprue (flash) during withdrawal from the storage box.

In accordance with a further feature of the present invention, the footings extend in elongation of and planar with the broadsides of the well so that essentially the whole broadside of the measuring vessel forms a contact surface and thus significantly enhances the mutual support of the measuring vessels. Preferably, the measuring vessel is of symmetric configuration to further contribute to a trouble-free automatic operation.

BRIEF DESCRIPTION OF THE DRAWING

The above and other objects, features and advantages of the present invention will now be described in more detail with reference to the accompanying drawing in which.

DETAILED DESCRIPTION OF A PREFERRED EMBODIMENT

Figure 1:
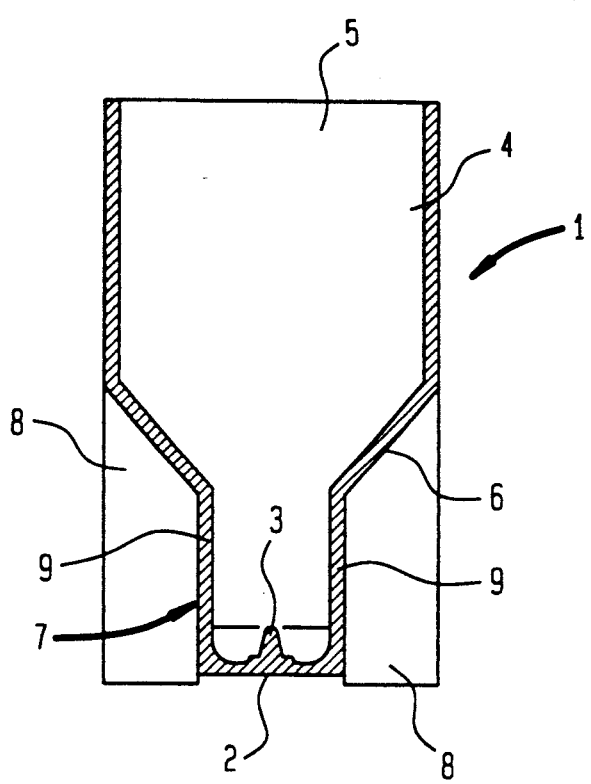
FIG. 1 is a front sectional view of a measuring vessel according to the present invention.
Figure 3:
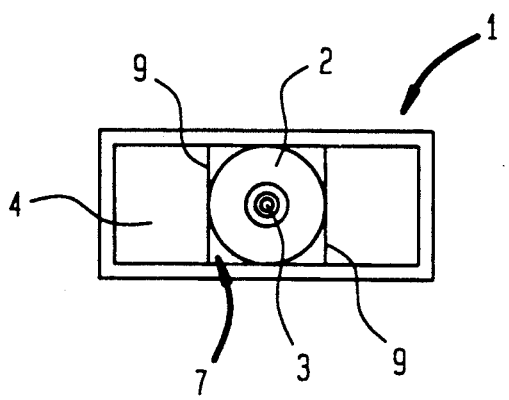
FIG. 3 is a schematic top view of the measuring vessel.

Referring now to the drawing and in particular to FIG. 1, there is shown a front sectional view of a measuring vessel according to the present invention, generally designated by reference numeral 1. The measuring vessel I is of generally rectangular outer configuration and includes a generally rectangular compartment or well 4 so as to define parallel broadsides forming planar contact or bearing surfaces. The well 4 terminates at its upper end in an inlet opening 5 through which fluid to be tested is introduced, and at its lower end in an outwardly flaring skirt or funnel 6 which is connected to a tubular member, generally designated by reference numeral 7. The lower end of the tubular member 7, opposite to the funnel 6, is closed by a circular bottom 2 (FIG. 3). The bottom 2 is integrally provided with an inwardly projecting central limiter pin 3 and defines a track for a spherical body (not shown) for determination the coagulation behavior of the fluid in accordance with the "ball method".

In the non-limiting example of FIG. 1, the tubular member 7 is of square configuration and has at least two opposing side faces 9 which are oriented parallel to each other and extend in the inner area just short of the entire length 1 of the tubular member 7. In the lower bottom area, the tubular member 7 is of cylindrical configuration, with the bottom 2 being trough-shaped in the area between the limiter pin 3 and the peripheral cylindrical side wall so as to enable the spherical body to roll along the thus-formed track.

The inside diameter d of the bottom 2 and thus of the cylindrical area of the tubular member 7 corresponds to the inner width w of the whole measuring vessel 1 and thus to the inner length 1 the sides of the square tubular member 7, as shown in the drawings.

Figure 2:
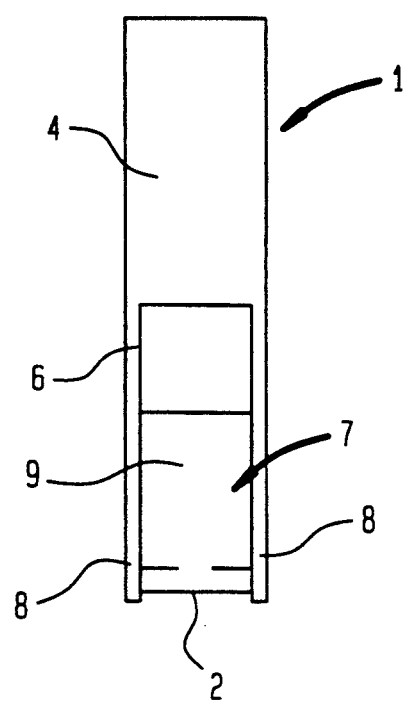
FIG. 2 is a side view of the measuring vessel.

In order to increase the stability of the measuring vessel 1, in particular during automatic transport to an analyzer, a support structure is provided in form of footings 8 which extend in elongation of the outer edge of the broadsides of the well 4 and are connected to the respective sides of the tubular member 7, as best seen in FIGS. 1 and 2. Thus, each footing 8 forms together with the associated upwardly continuing side face of the well 4 a broadside of the measuring vessel 1. Suitably, the footings 8 project slightly beyond the bottom 2 because flash or sprue remaining attached to the molded vessel may otherwise interfere during withdrawal of the vessel from the storage box.

While the invention has been illustrated and described as embodied in a measuring vessel, it is not intended to be limited to the details shown since various modifications and structural changes may be made without departing in any way from the spirit of the present invention. What is claimed as new and desired to be protected by Letters Patent is set forth in the appended claims.

I claim:

1. A measuring vessel for containment of liquids to be tested comprising:
    a rectangular well having one end defining an inlet opening and another end configured in form of a funnel, said well including parallel broadsides, each of which forming a planar contact surface;
    a tubular member having one end connected to said funnel-shaped end of said well and another end closed by a cylindrical bottom with a projecting central limiter pin to define a track for a spherical body for allowing determination of a coagulation behavior of the liquid, said tubular member being defined by a length and including at least two parallel side faces extending over a major portion of the length of said tubular member; and
    support means connected to said tubular member for enabling a secure placement of the measuring vessel.

2. A measuring vessel as defined in claim 1 wherein said tubular member is of square cross section.

3. A measuring vessel as defined in claim 1 wherein said cylindrical bottom has an inside diameter and said tubular member has a inner side length, said inside diameter of said bottom corresponding to the inner side length of said tubular member.

4. A measuring vessel as defined in claim 1 wherein said support means includes a lateral footing in prolongation of each broadside of said well.

5. A measuring vessel as defined in claim 1 wherein each of said broadsides of said well defines an outer edge, said support means extending to said outer edge of said broadsides.

6. A measuring vessel as defined in claim 1 wherein said support means extends slightly beyond said bottom.

7. A measuring vessel as defined in claim 1 wherein said support means extends planar with said broadsides of said well.

* * * * *